(12) United States Patent
Redl

(10) Patent No.: US 6,620,125 B1
(45) Date of Patent: Sep. 16, 2003

(54) METHOD AND DEVICE FOR MIXING AND APPLYING COMPONENTS OF DIFFERING VISCOSITIES

(75) Inventor: Heinz Redl, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/527,973

(22) Filed: Mar. 17, 2000

(51) Int. Cl.[7] ............................................. A61M 37/00
(52) U.S. Cl. ....................... 604/83; 222/145.6; 604/191
(58) Field of Search ................. 604/83, 191; 222/145.6

(56) References Cited

U.S. PATENT DOCUMENTS

| | | | | |
|---|---|---|---|---|
| 2,816,518 A | * | 12/1957 | Daggett | 222/145.6 |
| 4,359,049 A | * | 11/1982 | Redl et al. | 604/191 |
| 4,631,055 A | * | 12/1986 | Redl et al. | 604/191 |
| 4,978,336 A | * | 12/1990 | Capozzi et al. | 604/191 |
| 4,979,942 A | * | 12/1990 | Wolf et al. | 604/83 |
| 5,116,315 A | * | 5/1992 | Capozzi et al. | 604/191 |
| 5,814,022 A | * | 9/1998 | Antanavich et al. | 604/191 |
| 6,047,861 A | * | 4/2000 | Vidal et al. | 222/145.5 |
| 6,161,730 A | * | 12/2000 | Heusser et al. | 222/145.6 |
| 6,328,229 B1 | * | 12/2001 | Duronio et al. | 222/145.5 |

* cited by examiner

Primary Examiner—Gerald A. Michalsky
(74) Attorney, Agent, or Firm—Stradling Yocca Carlson & Rauth; Jeffrey C. Nichols

(57) ABSTRACT

A method and a device for mixing at least two liquid components of different viscosities of a multi-component material, such as a tissue adhesive, during application thereof, are disclosed, the components being pressed out of separate containers, mixed, and applied by aid of an application part, e.g. a cannula, the less viscous component being directly pressed into the flow of at least one other, more viscous component.

14 Claims, 5 Drawing Sheets

METHOD AND DEVICE FOR MIXING AND APPLYING COMPONENTS OF DIFFERING VISCOSITIES

FIELD OF INVENTION

The invention relates to a method for mixing at least two liquid components of different viscosities of a multi-component material, such as a tissue adhesive, during application thereof, the components being pressed out of separate containers, mixed, and applied by aid of an application part, e.g. a cannula.

Furthermore, the invention also relates to a device for mixing at least two liquid components of different viscosities of a multi-component material, such as a tissue adhesive, during application thereof, said device comprising separate component entrances provided in spaced relationship from each other, a mixing region, and an exit.

BACKGROUND

From AT 379 311 B, a device for applying a tissue adhesive is known in which the two components of the tissue adhesive, i.e. thrombin, on the one hand, and fibrinogen, on the other hand (or, strictly speaking, solutions thereof), by means of a double-syringe reach a device designed as a one-piece collecting head or connecting head, where the two components are supplied to a mixing cannula, or a mixing catheter via separate channels, together with a gas used for mixing. In the mixing cannula, or mixing catheter, respectively, thus the two components are mixed if required; in doing so, the gas is continuously supplied so as to keep clear the individual conveying channels whenever the tissue adhesive components are not being supplied.

A device for applying a multi-component tissue adhesive which is similar as regards mixing of the components by using a gas furthermore is known from EP 669 100 A, that device being provided for spray application of the tissue adhesive. To this end, the components are mixed immediately downstream of the front side of the connecting body designed with various channels, and atomized by aid of a medicinal gas.

In contrast to these known devices, more and more often a mixture of the components without the assistance of a medicinal gas is desired. Thorough mixing of the components without an early clot formation causing blocking of the passages poses substantial problems. From U.S. Pat. No. 5,116,315 A, a double syringe is known which has a connecting head having entrances connected to the delivery ends of the syringes and having a forward end side facing away from the syringes provided with a conical spray top latchingly engaging with the connecting body and in which a flat, disk-shaped mixing space is formed into which the conveying channels for the tissue adhesive components end at the outer periphery thereof, and from which centrally an axial exit leads away. On this top, a cannula, e.g., can be put. The design of this device may allow formation of clot within the device which would lead to clogging.

It is now an object of the invention to eliminate these problems and to provide a method and an arrangement, respectively, of the initially defined kind with which a reliable mixing of the components of a multi-component material is obtained without premature solidification, wherein also the supply of a medicinal gas is no longer necessary.

BRIEF DESCRIPTION OF THE INVENTION

The method according to the present invention is characterized in that the less viscous component is directly pressed into the jet or flow of at least one other component having a higher viscosity.

In corresponding manner, the device of the present invention is characterized in that the entrance for the less viscous component is followed by a guiding part for pressing the less viscous component directly into a flow passage for the more viscous component, which flow passage leads from the entrance to the exit.

According to the present invention, thus, the less viscous component is actively pressed into the other, more viscous component, e.g. by injecting a jet of the less viscous component directly into the jet or flow of the more viscous component. This ensures good mixing of the two components, the more viscous component being entrained by the less viscous component—which preferably is pressed in at an approximately right angle to the flow direction of the more viscous component. Since subsequently the component jet or flow may immediately be supplied to the exit or to the applicator tip respectively, with dead spaces being avoidable without any problem, undesired clot formation is avoided. Before the less viscous component is pressed into the jet or flow of the more viscous component, the less viscous component may deliberately be delayed so that the two components will arrive practically simultaneously in the mixing region despite the higher flow rate of the less viscous component due to its lower viscosity. This delay could as such be attained by a delayed supply of the component to the entrance, e.g. by a delayed pressing out of a syringe body as compared to the other, more viscous component. As regards the device itself, an embodiment of the device according to the invention which is particularly advantageous as regards such a delay is characterized in that the guiding part simultaneously defines a delaying path for the less viscous component. Here, the guiding part will guide the less viscous component on a longer path, the delaying path, as far as to the flow passage for the highly viscous component, i.e. the flow paths for the different components of the multi-component material are differently configured.

In connection with the delay of the less viscous component, it may also be suitable if the entrance for the less viscous component has a smaller passage cross-section than the entrance for the more viscous component. Namely, if the piston paths from the commonly used syringe bodies are equal at a simultaneous actuation of the syringe pistons and corresponding component amounts are pressed out, by the narrowing of the entry channel for the less viscous component, i.e. the smaller passage cross-section, a higher velocity and thus energy of the less viscous component can be attained so that the latter, despite a longer flow time caused by the delay on or in the guiding part, respectively, nevertheless will enter into the jet or flow of the highly viscous component with a sufficiently high energy so as to ensure thorough mixing.

Preferably, the less viscous component is delayed as mentioned before, by being detoured, or deflected, respectively, so as to compensate the lower flow velocity of the other component given on account of its higher viscosity. Preferably, the jet of the less viscous component can be deflected on a guiding surface or impacting surface for the purpose of retarding it. In doing so, the jet of the less viscous component impacts on the guiding or impacting surface and is deflected by the latter to the preferably substantially straight-line jet or flow of the more viscous component.

On the other hand, however, it is also possible to attain the delay by pressing the jet of the less viscous component into a blind tube arranged adjacent the jet or flow of the more viscous component and having at least one lateral nozzle opening at a distance from the forward, closed end face and through at least one lateral nozzle opening into the jet or flow of the more viscous component. The less viscous component enters the blind tube, passes as far as to the closed forward end face and only then emerges through at least one lateral nozzle opening so as to get into the jet or flow of the more viscous component. By the length of the blind portion of the tube, i.e. the distance of the nozzle opening(s) from the forward, closed end face, the time of the delay can be fixed.

An advantageous embodiment of the device according to the invention is characterized in that the guiding part defines an angularly arranged, optionally curved guiding face for deflecting the jet of the less viscous component towards the flow passage for the more viscous component. On the other hand, in terms of construction, it may advantageously be provided that a blind tube is provided as a guide part adjacent the flow passage for the more viscous component, which blind tube, at a distance from its forward, closed end face, has at least one nozzle opening ending in the flow passage for the more viscous component, the blind tube being connected with the inlet for the less viscous component. The flow passage for the more viscous component may also be formed by a cannula or a cannula holder, by a flexible tube or also by a channel in a connecting head.

The device according to the present invention may advantageously comprise a one-piece collecting or connecting head with a connecting part for a cannula or a catheter, in particular a double lumen catheter, the guiding part being provided in the region of the connecting part. For a simple production it is particularly advantageous if the guiding face is moulded to the forward end face of the connecting head and opens towards the mixing region which is outwardly delimited by a cannula holder slipped thereto. For completing the application device, preferably the entrances of the device moreover are connected with discharge parts of syringe bodies; in this case, the syringe bodies contain the different components of the multi-component material.

In the following, the invention will be explained in more detail by way of advantageous exemplary embodiments illustrated in the drawings, to which, however, it shall not be restricted.

DETAILED DESCRIPTION OF PREFERRED EMBODIMENTS

Figure 1:
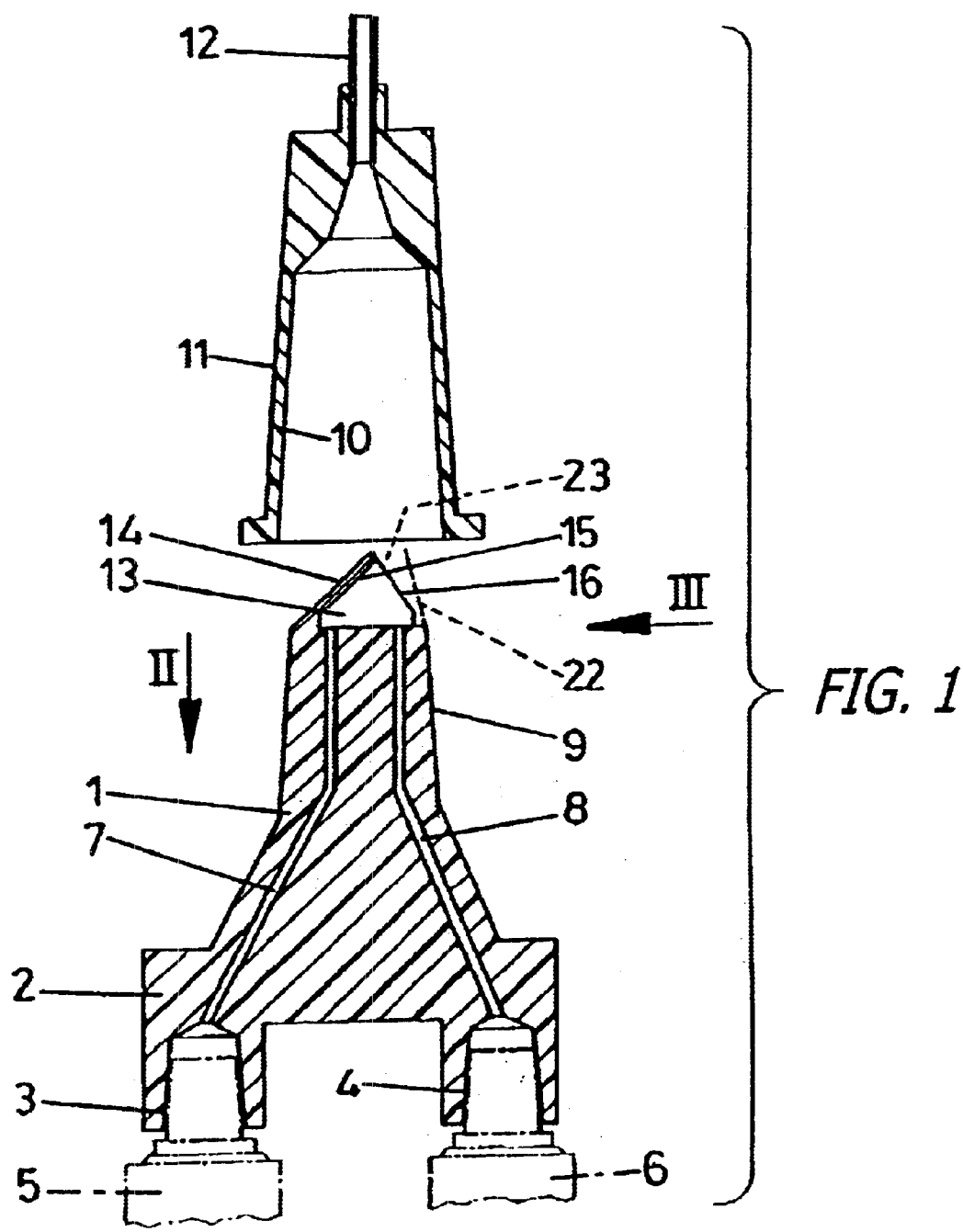
FIG. 1 shows an exploded view of a device for mixing the components of a tissue adhesive, comprising a one-piece connecting head and a cannula holder which can be slipped thereto and includes a cannula, these two parts being illustrated in section; in addition, in FIG. 1 the ends of syringe bodies in which the tissue adhesive components are contained are shown in dot-and-dash lines.

As an essential element, the mixing device according to FIG. 1 comprises a one-piece, synthetic material injection-moulded connecting head 1 which has a joining part 2 with plug-in coni 3 which are, or will be, put on Luer-type coni 4 of first syringe body 5 or second syringe body 6, respectively. The connecting head 1 is provided with first channel 7, and second channel 8 in the form of channels leading away from plug-in coni 3 and provided for the different components contained in the first syringe body 5, and second syringe body 6 to be mixed with each other; in particular, the components are tissue adhesive components, i.e. a fibrinogen component which has a relatively high viscosity and is contained in second syringe body 6, and from there gets to second channel 8, and a thrombin component of relatively low viscosity which is contained in first syringe body 5 and is pressed via first channel 7 through the connecting head 1.

The first and second channels 7 and 8, respectively, continue through the connecting head 1 as far as to its connecting part 9, which, on its outer side, is slightly conically designed and acts as a slip-on conus for the inner conus 10 of a cannula holder 11. The cannula holder 11 in a per se common manner carries a cannula 12 only partly illustrated in FIG. 1. Just like the connecting head 1, the cannula holder 11 may also be made in one piece of a synthetic material conventionally used in medicine, such as, e.g., a polyolefin (polyethylene, polypropylene), polyurethane, PVC or ABS (acrylonitrile-butadiene-styrene). These parts 1, 11 preferably may be injection moulded.

Figure 2:
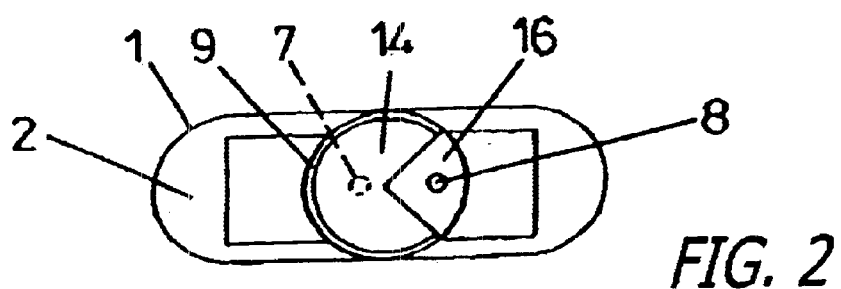
FIG. 2 shows a top view onto the connecting head according to line II of FIG. 1.
Figure 3:
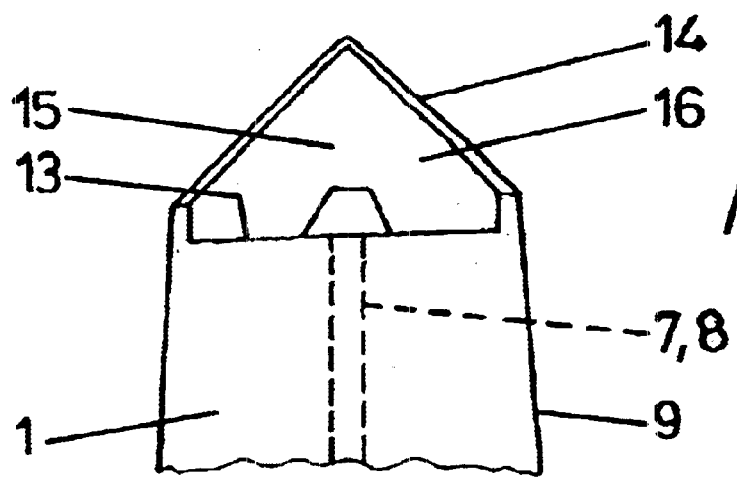
FIG. 3 shows a side view of a front-side end region of the connecting head according to line III in FIG. 1, to illustrate the conical, roof-shaped guiding part at the end side of the connecting head.

To the end side of the connecting head 1, following the end face 13, where first and second channels 7, 8 have their exits, a guiding part 14 is moulded which has the shape of a cut-off cone, its inner side constituting a guiding face 15 to the thrombin component jet emerging from first channel 7. The cut-out of the conical guiding part 14 which has the shape of a quarter-circle sector, is particularly visible from FIG. 2 in top view at 16, cf. also FIGS. 1 and 3.

Figure 4:
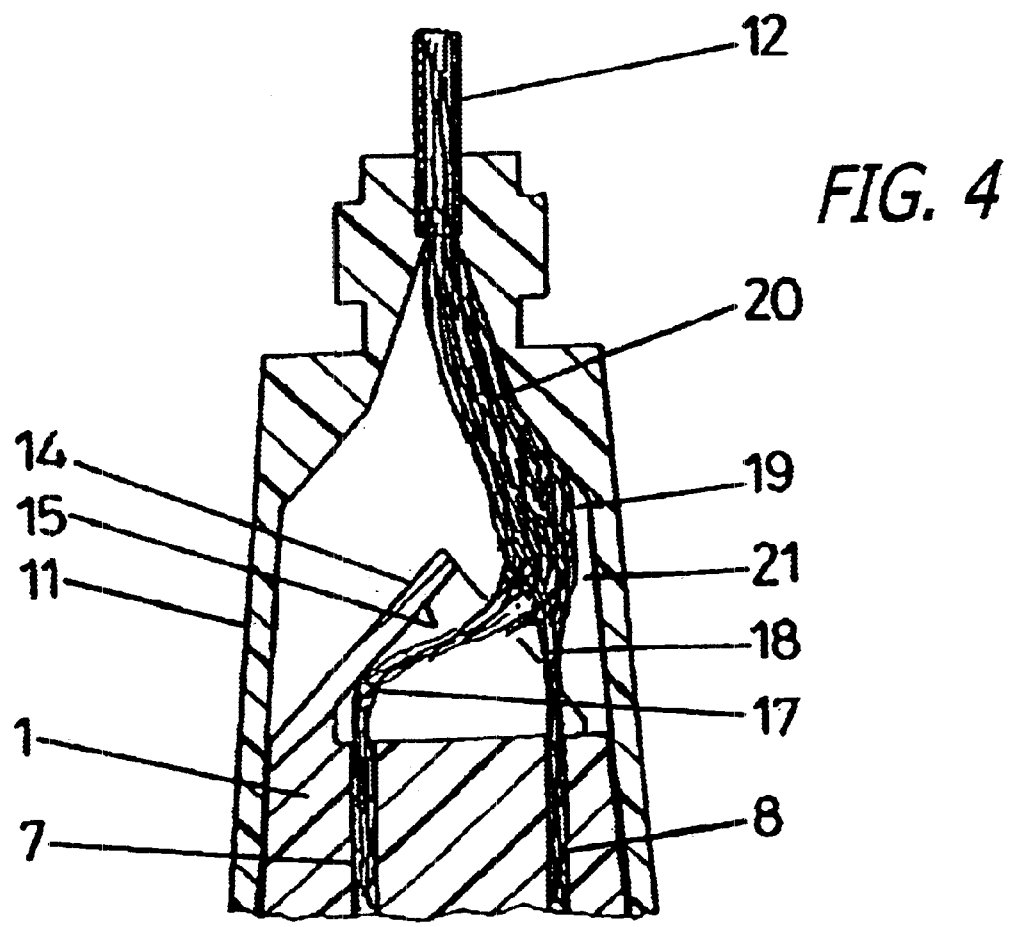
FIG. 4 shows the region of the connecting head with the guiding part and the slipped-on cannula holder in section, to illustrate the mode of action of the present device.

In FIG. 4, that region of the present device which is essential for mixing of the two components is illustrated in the instance of operation. Through second channel 8, the fibrinogen component is forced, and through first channel 7, the thrombin component is forced, in conventional manner by inward movement of syringe pistons not illustrated in FIG. 1 into first and second syringe bodies 5, 6. In FIG. 4, the jet of the thrombin component, in general the less viscous component, is illustrated at 17, and the jet or flow of the fibrinogen component is illustrated at 18. In a mixing region 19, these two components are mixed, i.e. by deflecting the comparatively less viscous component 17 on the guiding face 15 of the guiding part 14 and actively introducing or pressing it with a certain energy into the jet of flow 18 of the more viscous component. By this deflection or detour of jet 17 on the guiding face 15, a delaying path is obtained so that the less viscous component is also somewhat delayed, whereby the flow velocity of the less viscous component, which is higher as compared to the more viscous component 18 is equalized; accordingly, at the onset of the mixing procedure, both components 17, 18, can practically arrive simultaneously in the mixing region 19. From the mixing region 19, a flow 20 of the mixed components then will extend through the interior of the cannula holder 11 towards the cannula 12, as is apparent from FIG. 4.

Thus, in the exemplary embodiment according to FIGS. 1 to 4, the cannula holder 11 with its inner wall defines a flow passage 21 for the mixing region 19, which is provided on the other side, adjacent the guiding part 14. In an alternate embodiment it would, of course, also be possible to entirely accommodate the mixing region 19 within the connecting head 1, e.g. by providing a wall at the side of the connecting head opposite the guiding part 14 as indicated in dashed lines at 22 in FIG. 1, in which case the upper opening remaining between the guiding part 14 and this wall 22 will define an alternate exit 23. In the embodiment according to FIG. 4, the cannula 12 de facto forms the exit.

In the embodiment according to FIG. 5, again a cannula holder 11 delimits the mixing region 19 or an alternate flow passage 24 for the more viscous component, respectively, cf. arrow 18, into which the less viscous component is pressed in. Again, a connecting head 1' is provided which has first and second channels 7, 8 for the two components. The first channel 7 for the less viscous component (thrombin) is followed by a tube 25 which is closed at its forward end 26 so that a blind tube portion 27 is provided as guiding part for the less viscous component. This blind tube portion 27 forms a dam-up portion extending from nozzle openings 28 in the tube 25 to the closed forward end 26; through the nozzle openings 28, the less viscous component is pressed out after the blind tube portion 27 has been filled, cf. also the transversely extending arrows in FIG. 5. In this manner, again the less viscous component is actively pressed with a delay, caused by filling of the blind tube portion 27, into the flow of the more viscous component indicated by arrow 18 in the flow passage 21 within the cannula holder 11. Otherwise, the embodiment of the mixing device according to FIG. 5 corresponds to the embodiment according to FIGS. 1 to 4, primarily as regards the connecting part 2 of the connecting head 1' for connection with first and second syringe bodies 5, 6, as well as for applying the mixed components through the cannula 12.

Figure 5:
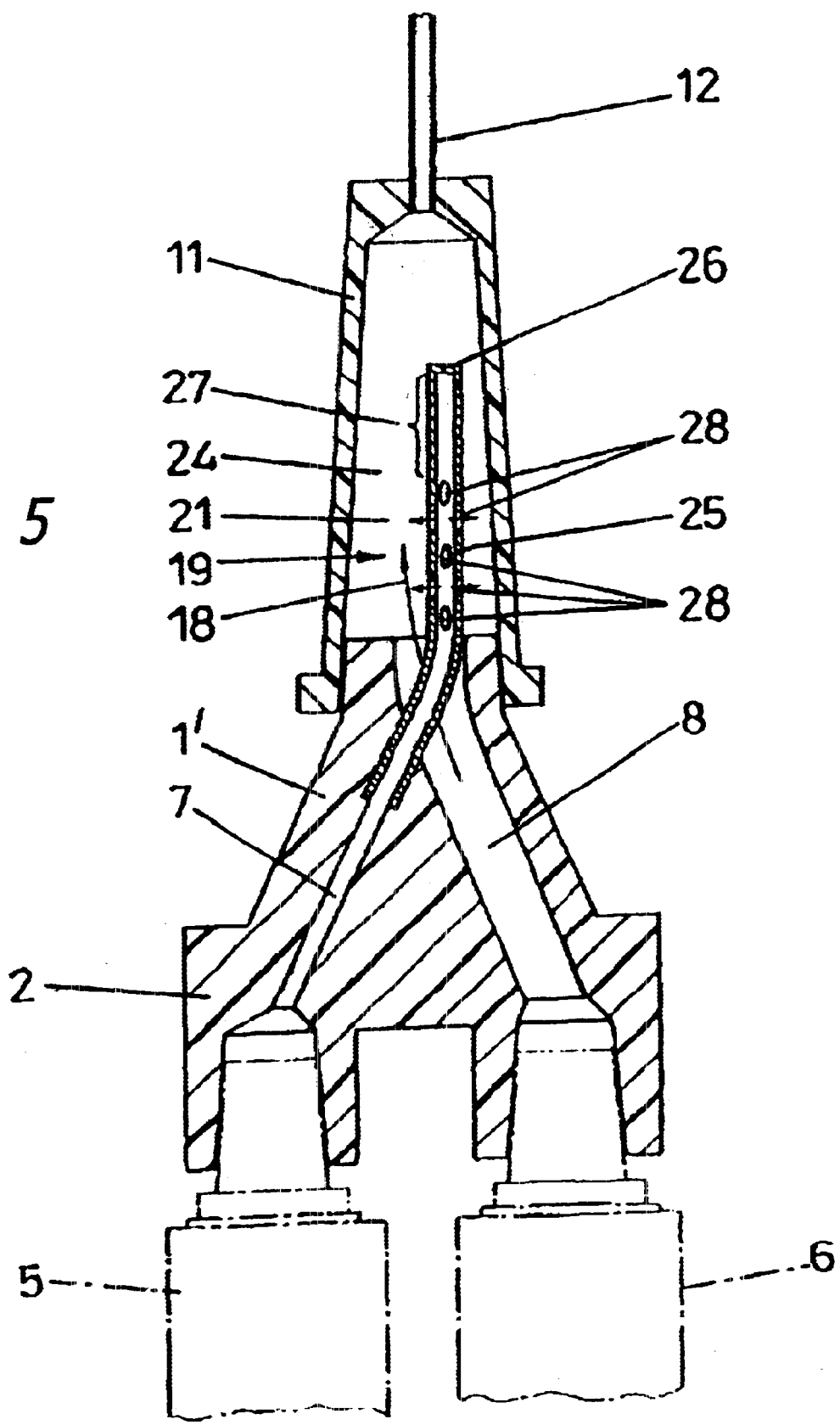
FIG. 5 shows a section of a further mixing device including a connecting head and a cannula holder.
Figure 6:
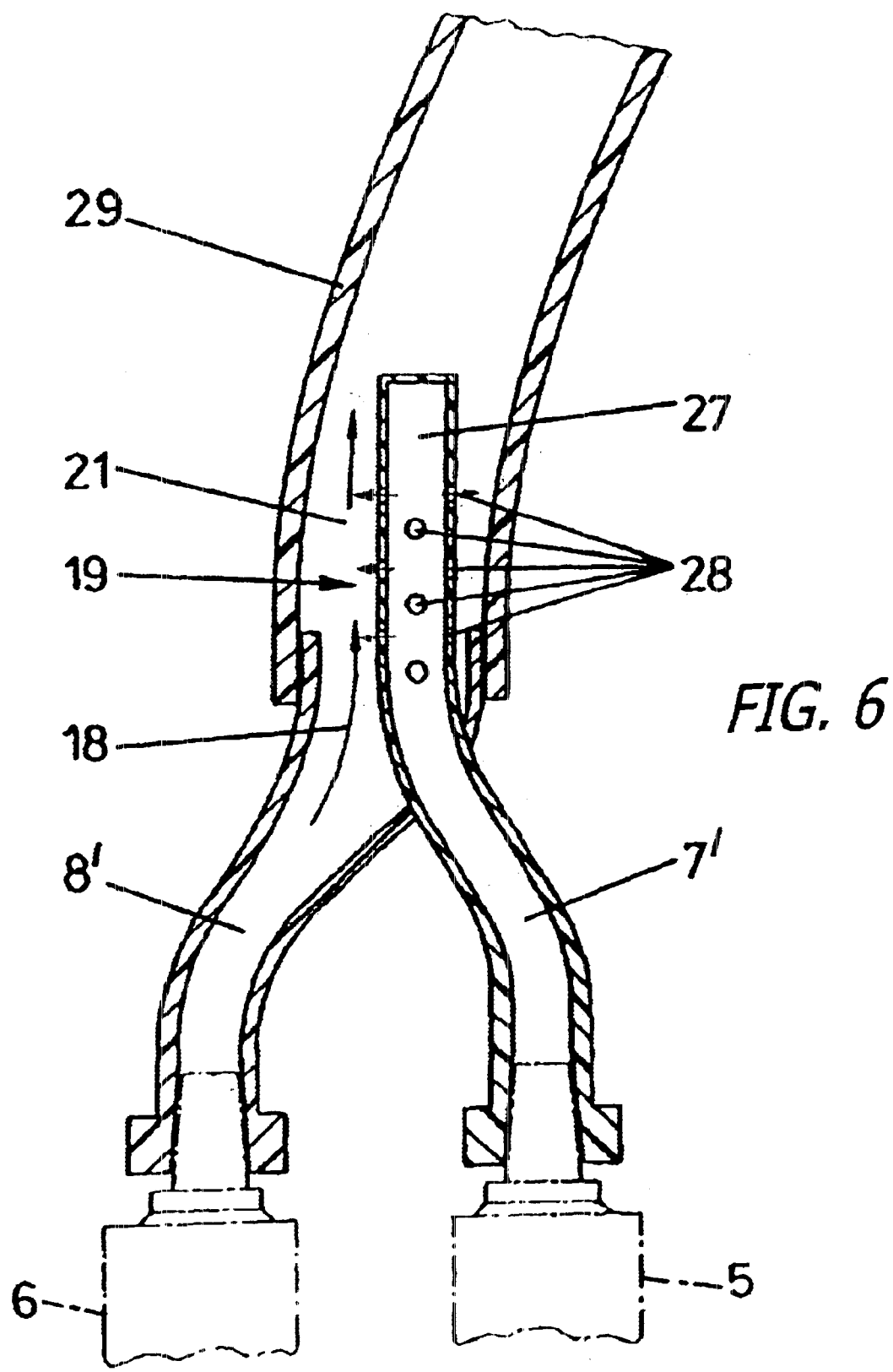
FIG. 6 shows yet another, present particulary preferred mixing device, in this instance with a slipped-on catheter in a comparable sectional representation.

The device according to FIG. 6 is similar to that according to FIG. 5 as regards the provision of a blind tube portion 27, yet it differs from that according to FIG. 5 in that instead of a synthetic material connecting head, first and second ducts 7', 8' for the two components are provided which are guided one within the other, the first duct 7' merging into the blind tube portion 27, with nozzle openings 28 being provided in the preceding region. The two ducts 7', 8' are slipped onto the Luer-type coni of syringe bodies 5, 6, and a catheter tube 29, e.g., is put on second duct 8' which is provided for the highly viscous component. This catheter tube 29 forms the flow passage for the highly viscous component following second duct 8', and in combination with the latter it also defines the mixing region 19, where the less viscous component, after a time delay caused by filling of the blind tube portion 27, is pressed into the flow 18 of the more viscous component through the nozzle openings 28.

Figure 7:
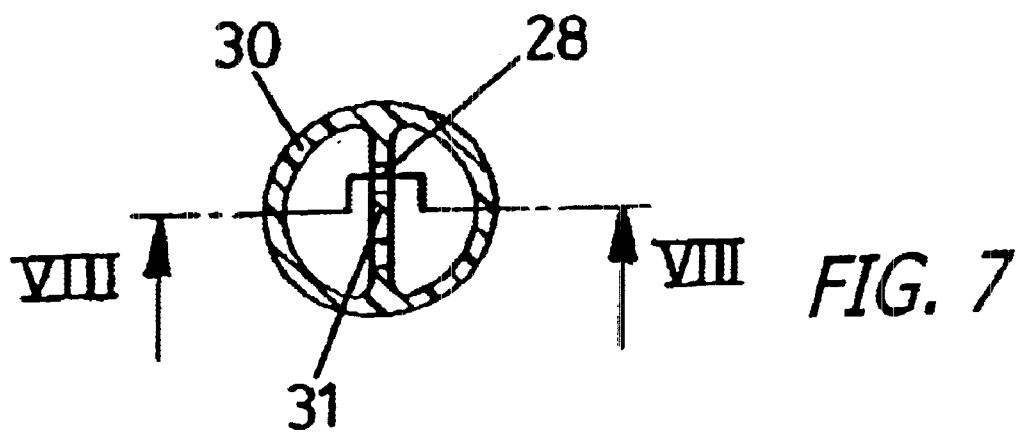
FIG. 7 shows a cross-section through a fourth embodiment of the present mixing device, according to line VII—VII of FIG. 8.
Figure 8:
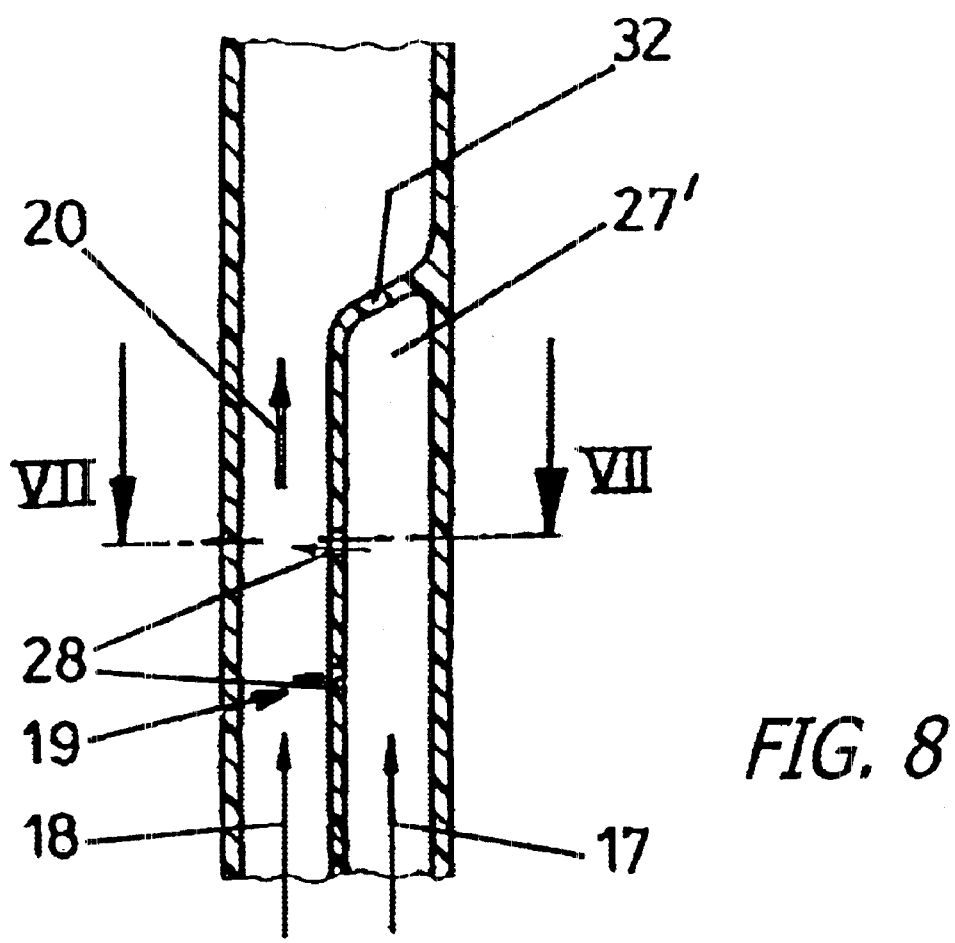
FIG. 8 shows an axial section through the essential part of this mixing device of FIG. 7, in accordance with line VIII—VIII of FIG. 7.

Also in the embodiment according to FIGS. 7 and 8, a blind tube portion 27' is provided to delay the less-viscous component (cf. arrow 17) relative to the more viscous component 18. In detail, in this embodiment a tube-shaped part 30, e.g. of synthetic material, is provided which may, e.g., form an extension of a connecting head 1 or 1' according to FIGS. 1 to 4 or 5, and which inwardly is subdivided as far as to the closed end 32 of the blind tube portion 27' by a separating wall 31 so as to form separate flow passages for the two components of different viscosities, cf. arrows 17 and 18. In the separating wall 31, again nozzle openings 28 are provided at a distance in front of the closed end 32, through which the less viscous component 17, after having been delayed, e.g. after filling of the blind tube portion 27', is pressed out and actively pressed into the flow 18 of the more viscous liquid; the mixing region therefor again is indicated by 19. Subsequently, the component mixture continues to flow at 20 in tube-shaped part 30, e.g. to a cannula not illustrated in detail or to a catheter not illustrated in detail, either.

Further modifications for pressing the less viscous component with delay into the jet of the more viscous component are conceivable, such as particularly that such pressing in is effected directly in the interior of a collecting head; in this case it is also conceivable that the collecting head provides for a spray application of the mixture at its end side (instead of application via a cannula or a catheter). Moreover, it is also conceivable to provide the mixing space 19 directly within a cannula, e.g. by lengthening the second duct 8' to a cannula in the embodiment according to FIG. 6.

In a further embodiment, pressing in of the less viscous component into the more viscous component is effected in the application part itself, i.e., e.g., in a cannula or needle, in particular in such an exchangeable part. This means that within the application part itself, a means for pressing in, e.g. a deflection means, may be provided. After a single use of the device, the respective application part may simply be exchanged and replaced by a new part.

In a further embodiment, the device comprises at least one further channel. The latter may, e.g., be used for supplying a gas, e.g. air or $CO_2$, or for cleaning the device or the application part, respectively. The device may also comprise two further channels, wherein one channel serves to supply a gas and the second channel serves for cleaning the device. By supplying a gas, in particular the components to be mixed are sprayed, e.g. directly onto the wound area to be treated.

For special embodiments of the device, such as e.g., that of a catheter, also a pressure regulating means may be provided for the gas supply. Cleaning of the device from contaminations or deposits that have formed, such as, e.g., clot formations which form by mixing thrombin and fibrinogen, may, e.g., be effected by simple sucking off by means of a vacuum in the additional channel. Cleaning may also be effected by other methods known from the prior art.

What is claimed is:

1. A device for mixing at least two liquid components of a multi-component material, comprising:
   a first component channel and at least a second component channel provided in spaced relationship from each other;
   a guiding part for directing a flow of a less viscous component directly from the first channel into a flow of a more viscous component from said second channel;
   a mixing region in communication with said first and at least the second component channel; and
   an exit in communication with said mixing region.

2. A device according to claim 1, wherein said guiding part defines a delay path for said less viscous component.

3. A device according to claim 1, wherein said first channel for the less viscous component has a smaller passage cross-section than said at least one separate channel containing said more viscous component.

4. A device according to claim 1, wherein said guiding part defines an angularly arranged guiding face, said guiding face capable of directing said flow of said less viscous component into said flow of said more viscous component.

5. A device according to claim 4, further comprising a forward end face integral with said guiding face positioned within a connecting head, said guiding face opening towards a mixing region formed in said connecting head, said connecting head outwardly delimited by a cannula holder attachable thereto.

6. A device according to claim 1, comprising a blind tube portion connected to said first channel receiving said less viscous component, said blind tube portion located adjacent to said at least one separate channel containing said more viscous component, said blind tube having at least one nozzle opening within said at least one separate channel containing said more viscous component.

7. A device according to claim 6, wherein said at least one separate channel containing said more viscous component is formed by a cannula.

8. A device according to claim 6, wherein said at least one separate channel containing said more viscous component is formed by a catheter tube.

9. A device according to claim 6, wherein said at least one separate channel containing said more viscous component is formed by a channel formed in a connecting head.

10. A device according to claim 1, further comprising:
a one-piece connecting head attached to a connecting part; and
a cannula holder attachable to said one-piece connecting head, said cannula holder attachable to a cannula and having said guiding part provided thereon.

11. A device according to claim 1, wherein the first and second channels are connected with Luer-type coni of a first syringe body and a second syringe body, respectively.

12. The device of claim 1, wherein said guiding part further comprises a guiding face having substantially straight surface.

13. The device of claim 1, wherein said guiding part further comprises a guide face having a curved surface.

14. A device for mixing at least two liquid components of a multi-component material, comprising:
a body having a first component channel and at least a second component channel positioned in spaced relation to each other formed therein;
a guiding part positioned within said body and in communication with a first component channel, said guiding part capable of directing a flow of a first component from said first channel into a flow of at least a second component from at least said second channel;
a mixing region in communication with said first component channel and at least said second component channel; and
an exit in communication with said mixing region.

* * * * *